United States Patent
Widdison et al.

(10) Patent No.: US 7,411,063 B2
(45) Date of Patent: Aug. 12, 2008

(54) PROCESS FOR PREPARATION OF MAYTANSINOL

(75) Inventors: Wayne C. Widdison, Sommerville, MA (US); Ravi V. J. Chari, Newton, MA (US)

(73) Assignee: Immunogen, Inc., Waltham, MA (US)

( * ) Notice: Subject to any disclaimer, the term of this patent is extended or adjusted under 35 U.S.C. 154(b) by 73 days.

(21) Appl. No.: 11/594,156

(22) Filed: Nov. 8, 2006

(65) Prior Publication Data

US 2007/0112188 A1    May 17, 2007

Related U.S. Application Data

(60) Provisional application No. 60/734,330, filed on Nov. 8, 2005.

(51) Int. Cl.
*C07D 491/12* (2006.01)
*C07D 498/06* (2006.01)
(52) U.S. Cl. ...................................................... 540/456
(58) Field of Classification Search ................... 540/456
See application file for complete search history.

(56) References Cited

U.S. PATENT DOCUMENTS 6,333,410 B1    12/2001    Chari et al.

*Primary Examiner*—Bruck Kifle
(74) *Attorney, Agent, or Firm*—Sughrue Mion, PLLC

(57) ABSTRACT

The present invention describes the preparation of maytansinol by methods that minimize processing steps, and reduce solvent volumes, making the process more efficient, and scaleable. This process comprises a step of converting bridged acetals of maytansinol to maytansinol. The simplified processing also aids in lowering the potential for human exposure to chemicals. Also provided is an isolated C3 to C9 bridged acetal of maytansinol.

48 Claims, 4 Drawing Sheets

Maytansinol

Ansamitocin P-2 R = Et, Ansamitocin P-3 R = iPr
Ansamitocin P-3' R= n-Pr Ansamitocin P-4 R = iBu
Ansamitocin P-4' R = nBu Maytansine R = CH₃
L-DM1 R = CH₂CH₂SH
L-DM4 R = CH₂CH₂(CH₃)₂SH unnatural N-methyl-D-alanine side chain
R = CH₃
D-DM1 R = CH₂CH₂SH
D-DM4 R = CH₂CH₂C(CH₃)₂SH Bridged acetal of Ansamitocin P-3

Ansamitocin P-3

Bridged acetal (I)

Maytansinol

US 7,411,063 B2

PROCESS FOR PREPARATION OF MAYTANSINOL

This application claims priority to U.S. Provisional Application No. 60/734,330, filed Nov. 8, 2005.

FIELD OF THE INVENTION

The present invention relates to improved processes for the preparation of maytansinol and to an isolated bridged acetal of a C3-ester of maytansinol.

BACKGROUND OF THE INVENTION

Maytansinoids are highly cytotoxic drugs. The first member of this class, maytansine, was isolated by Kupchan et al. from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al. *J. Med. Chem.* 21:31-37 (1978); Higashide et al. *Nature* 270:721-722 (1977); Kawai et al. Chem. Pharm. Bull. 32:3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters of maytansinol can be classified into two groups:
(a) Maytansine and its analogs described above, which are C-3 esters with N-methyl-L-alanine or derivatives of N-methyl-L-alanine (U.S. Pat. Nos. 4,137,230; 4,260,608; 5,208,020; and *Chem. Pharm. Bull.* 12:3441 (1984)); and
(b) Ansamitocins, which are C-3 esters with simple carboxylic acids (U.S. Pat. Nos. 4,248,870; 4,265,814; 4,308,268; 4,308,269; 4,309,428; 4,317,821; 4,322,348; and 4,331,598).

Ansamitocins are a mixture of compounds composed predominantly of ansamitocin P-2, ansamitocin P-3, ansamitocin P-3', ansamitocin P-4 and ansamitocin P-4', FIG. 1. The ansamitocin P-3 component of ansamitocins typically comprises over 70% of the total material in ansamitocins. Thus the mixture is often referred to as ansamitocin P-3. Ansamitocins are prepared by bacterial fermentation as described in U.S. Pat. Nos. 4,162,940, 4,356,265, 4,228,239, and 6,790,954.

Maytansine, its analogs, and each of the ansamitocin species are C3-esters of maytansinol that can be converted to maytansinol by cleavage of their respective ester side chains. Structures of maytansinols and several C3 esters are shown in FIG. 1. Typically, cleavage of the ester moiety is achieved through a reduction reaction. Thus, for example, C3-esters of maytansinol can be cleaved by treatment with lithium trimethoxyaluminum hydride (LATH) or by other alkali alkoxyaluminum hydrides at reduced temperatures, followed by quenching with water or an aqueous salt solution and extraction with organic solvent to give maytansinol, as described in U.S. Pat. No. 6,333,410. Maytansinol is the common starting material for the preparation of various maytansinoid drugs, as described in U.S. Pat. Nos. 4,322,348, 4,331,598 and 6,333,410. The processes of preparing maytansinol described thus far are tedious to perform and are time consuming, because the aluminum-based byproducts of the reduction can form suspensions or gels that are difficult to extract and that can retain significant amounts of product. Anderson, N. "Practical Process Research & Development" (2000) ISBN # 0-12-059475-7 pages 72.

SUMMARY OF THE INVENTION

The present invention pertains to improved methods to prepare maytansinol by the reduction of C3-esters of maytansinol. The methods result in improved yields of maytansinol by minimizing the formation of undesired side products. Simplified processing also aids in lowering the potential for human exposure to hazardous chemicals.

A surprising finding leading to this invention is that a major undesired by-product formed during the reduction of C3-esters of maytansinol, such as ansamitocins, with an aluminum-based hydride reducing agent, such as $LiAlH_4$ or $LiAl(OMe)_3H$, is a C3 to C9 bridged acetal of maytansinol. Thus, the invention describes a process to prepare maytansinol substantially free of bridged acetal from C3-esters of maytansinol. Reduction of C3-esters of maytansinol is carried out as described in U.S. Pat. No. 6,333,410, followed by an aqueous quench, which gives a basic mixture. Following the quench, this invention adds an important holding step. The holding step comprises maintaining the quenched mixture at a suitable temperature for a suitable period of time to facilitate conversion of any bridged acetal to the desired maytansinol.

After the bridged acetal is converted to maytansinol, an aqueous base or an aqueous buffer can be added to the quenched mixture to thereby minimize any decomposition of maytansinol and a water immiscible solvent is added to precipitate undesired aluminum-based byproducts of the reducing agent. Alternatively, any undesired aluminum-based byproducts can be solubilized by lowering the pH to about 2 or less.

Another aspect of the invention pertains to the isolation of the bridged acetal and also to methods of converting the isolated bridged acetal to maytansinol under basic or acidic conditions.

Accordingly, one aspect of the invention is a process for preparing maytansinol comprising:
a) reducing a C3-ester of maytansinol with an aluminum-based hydride reducing reagent;
b) quenching the reduction reaction; and
c) subjecting the quenched mixture to a holding step; wherein said holding step converts C3 to C9 bridged acetal into maytansinol.

Another aspect of the invention is an isolated C3 to C9 bridged acetal of a C3-ester of maytansinol.

A further aspect of the invention is a process for preparing an isolated C3 to C9 bridged acetal of a C3-ester of maytansinol comprising:
a) reducing a C3-ester of maytansinol with an aluminum-based hydride reducing agent;
b) quenching the reduction reaction, to thereby form a C3 to C9 bridged acetal of said C3-ester of maytansinol; and
c) isolating the bridged acetal.

An even further aspect of the invention provides an isolated C3 to C9 bridged acetal, which is a compound represented by Formula (I'):

Formula (I')

wherein:
X$_1$ represents H, Cl, or Br; X$_2$ represents H, or Me; X$_3$ represents H, Me, or Me(CH$_2$)pCOO, wherein p is between 0-10; and
R$_1$ represents alkyl, CH(CH$_3$)N(CH$_3$)Q, or CH(CH$_3$)N(CH$_3$)COR$_4$; Q represents H or an amino protecting group; and R$_4$ represents alkyl, aryl or (CH$_2$)$_n$(CR$_6$R$_7$)$_m$SV, in which n represents 0-9, m represents 0-2, provided m and n are not 0 at the same time, R$_6$ represents H, alkyl or aryl, R$_7$ represents H, alkyl or aryl, and V represents H or a thiol protecting group.

In a further aspect, the invention provides a compound represented by Formula (I), Formula (I)

wherein R$_1$ represents alkyl, CH(CH$_3$)N(CH$_3$)Q, or CH(CH$_3$)N(CH$_3$)COR$_4$; Q represents H or an amino protecting group; and R$_4$ represents alkyl, aryl or (CH$_2$)$_n$(CR$_6$R$_7$)$_m$SV, in which n represents 0-9, m represents 0-2, provided m and n are not 0 at the same time, R$_6$ represents H, alkyl or aryl, R$_7$ represents H, alkyl or aryl, and V represents H or a thiol protecting group.

DETAILED DESCRIPTION OF THE INVENTION

Figure 1A:
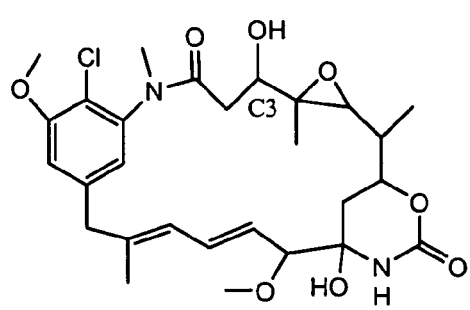
FIG. 1a shows the formula of maytansinol and FIG. 1b shows the formulas of the major ansamitocin species that are present in a mixture of ansamitocins isolated from bacterial fermentation.
Figure 1B:
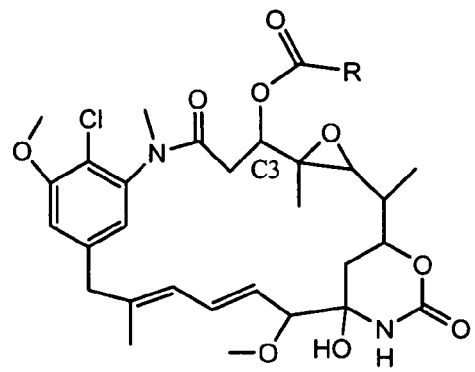
Figure 2:
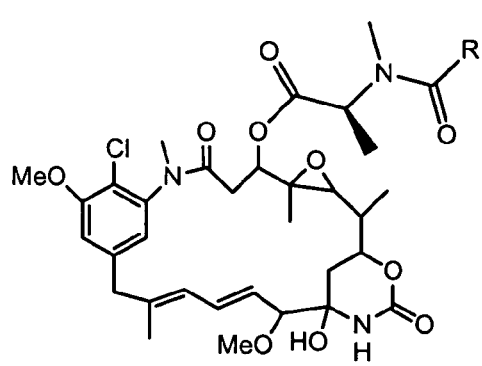
FIG. 2 shows the formula of maytansine and some of its analogs, and of maytansine analogs bearing the unnatural N-methyl-D-alanine moiety.
Figure 2:
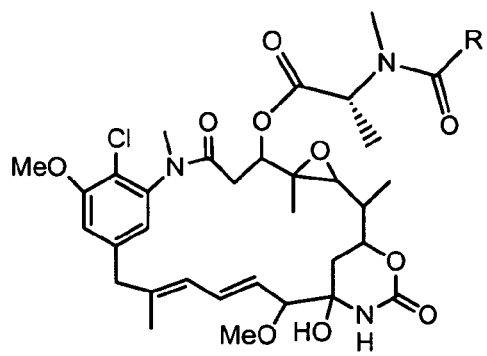
Figure 3:
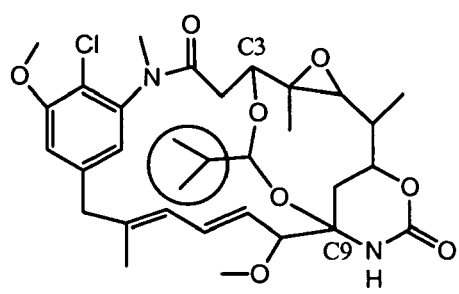
FIG. 3 shows the structural formula of the C3 to C9 bridged acetal species produced from reduction of ansamitocin P-3. The structural formula of ansamitocin P-3 is also shown for comparison. The acetal side chain of the bridged acetal and the ester side chain of ansamitocin P-3 are circled.
Figure 3:
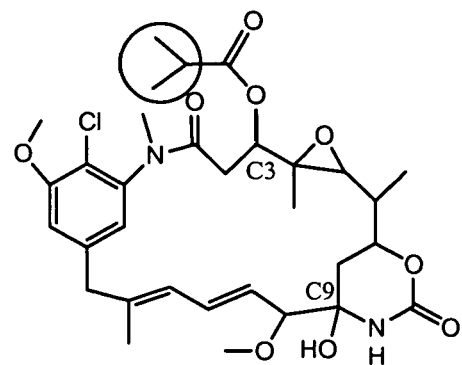

C3-Esters of maytansinol such as ansamitocins, maytansine, and derivatives of maytansine can be reduced by various aluminum-based hydride reducing agents, such as LiAlH$_4$ or LiAl(OMe)$_3$H at low temperature to give maytansinol as described in FIG. 2 of U.S. Pat. No. 6,333,410. Quenching of these reduction reactions with water or aqueous salts gives a highly basic mixture, i.e., a pH of greater than 11, that can cause significant decomposition of product if the mixture is allowed to warm. Attempts were made to avoid any decomposition of product by quenching the reaction with water and immediately adding acid to neutralize the pH before allowing the mixture to warm to room temperature. When this procedure was tried for the reduction of ansamitocins, a significant amount of a C3 to C9 bridged acetal of the C3 ester of maytansinol was obtained, resulting in a lower yield of the desired maytansinol. The side chain of the bridged acetal derived from reduction of the C3-ester of maytansinol was identical to the side chain of the C-3 ester, indicating that reduction of C3-esters of maytansinol gives a bridged acetal having the same side chain as that of the starting material, FIG. 3. Analysis of crude maytansinol samples produced by reduction of ansamitocins using the method described in U.S. Pat. No. 6,333,410 indicated that these samples also contained bridged acetal.

The invention describes a method to reduce C3-esters of maytansinol followed by a quench and a holding step, which allows any bridged acetal formed in the reduction to be converted to maytansinol. After conversion is complete, the pH of the mixture may be adjusted by addition of acid or aqueous buffer to avoid base induced decomposition of the maytansinol produced and to allow for precipitation of aluminum-based byproducts by adding a water immiscible solvent.

The starting material for the method of making maytansinol can be any naturally occurring or synthetic C3-ester of maytansinol and suitable analogues of maytansinol having a modified aromatic ring or modifications at positions other than the C3 position. Specific examples of suitable analogues of maytansinol having a modified aromatic ring include:
(1) C-19-dechloro (U.S. Pat. No. 4,256,746) (prepared by LAH reduction of ansamitocin P2);
(2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:
(1) C-9-SH (U.S. Pat. No. 4,424,219) (prepared by the reaction of maytansinol with H$_2$S or P$_2$S$_5$);
(2) C-14-alkoxymethyl (demethoxy/CH$_2$OR) (U.S. Pat. No. 4,331,598);
(3) C-14-hydroxymethyl or acyloxymethyl (CH$_2$OH or CH$_2$OAc) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322, 348) (prepared by the demethylation of maytansinol by *Streptomyces*); and (7) 4,5-deoxy (U.S. Pat. No. 4,371,533) (prepared by the titanium trichloride/LAH reduction of maytansinol).

As used herein, the phrase "C3-ester of maytansinol" includes suitable C3-esters of analogues of maytansinol, such as those described above. Any of the analogues described above and any other known analogues of maytansinol can have any of numerous known esters at the C3 position. Thus, one of ordinary skill in the art can readily envision numerous suitable C3-esters of analogues of maytansinol suitable for use as the starting material. Non-limiting Examples of C-3 esters of maytansinol include Antibiotic C-15003PND also known as C18-N-des-methyl-ansamitocin, (U.S. Pat. No. 4,322,348), 20-demethoxy-20-acyloxymaytansine (U.S. Pat. No. 4,294,757), 19-des-cloromaytansine and 20-demethoxy-20-acetoxy-19des-chloromaytansine (U.S. Pat. No. 4,294,757).

The step of reducing a C3-ester of maytansinol with an aluminum-based hydride reducing agent is well known in the art. Non-limiting examples of suitable aluminum-based hydride reducing agents include $LiAlH_4$, $LiAl(OMe)_3H$, sodium bis(2-methoxyethoxy)aluminum hydride, $LiAl(OMe)_{2.5}H_{1.5}$, and other alkali aluminum alkoxy hydrides prepared by addition of a non-stoichiometric amount of alcohol to an alkali aluminum hydride. $LiAl(OMe)_3H$ is preferred.

The temperature and other conditions for reduction of C3-esters of mayatnsinol are described in U.S. Pat. No. 6,333,410, which is incorporated herein by reference in its entirety.

After a suitable period of time readily determined by the skilled artisan, the reduction reaction is quenched with water or aqueous salts, also as described in the U.S. Pat. No. 6,333,410. This quench gives a mixture with a basic pH.

The C3 to C9 bridged acetals formed in the reduction reaction can then be converted to maytansinol by allowing the basic quenched mixture to stand during a holding period. The holding step comprises maintaining the quenched mixture at a suitable temperature for a suitable period of time to facilitate conversion of any bridged acetal to the desired maytansinol. Desirably, the holding step comprises maintaining the quenched mixture at a temperature of about $-15°$ C. to about $-50°$ C. for a period of at least about 0.25 and 5 hours or longer. The holding step under the basic conditions allows any bridged acetal formed during the reduction reaction to be converted to maytansinol. The time needed for the holding step under the above described conditions will depend on several factors, such as scale of the reaction, concentration, and extract temperatures and can be determined by monitoring the conversion of bridged acetal to maytansinol. For example, a sample aliquot of the reaction is withdrawn and analyzed. One skilled in the art would understand that samples can be prepared and analyzed by several methods, some of which include but are not limited to normal phase high performance liquid chromatography (HPLC), reverse phase HPLC and thin layer chromatography. In a representative case, ansamitocins are reduced with $LiAl(OMe)_3H$ then quenched with water. A small aliquot of the quenched reaction is added to a 0.3:0.05:1, water:acetic acid:ethy acetate (v:v:v) mixture. This essentially stops the conversion of bridged acetal to maytansinol. The organic layer of the test sample is analyzed to determine if the conversion of bridged acetal to maytansinol is complete or if the holding period must be extended. Ansamitocins, maytansinol and the bridged acetal are all separable by thin layer silica chromatography and by reverse phase HPLC. Analysis by either TLC or HPLC allows for monitoring of both the conversion of ansamitocins to the bridged acetals and the conversion of the bridged acetals to maytansinol.

Figure 4:
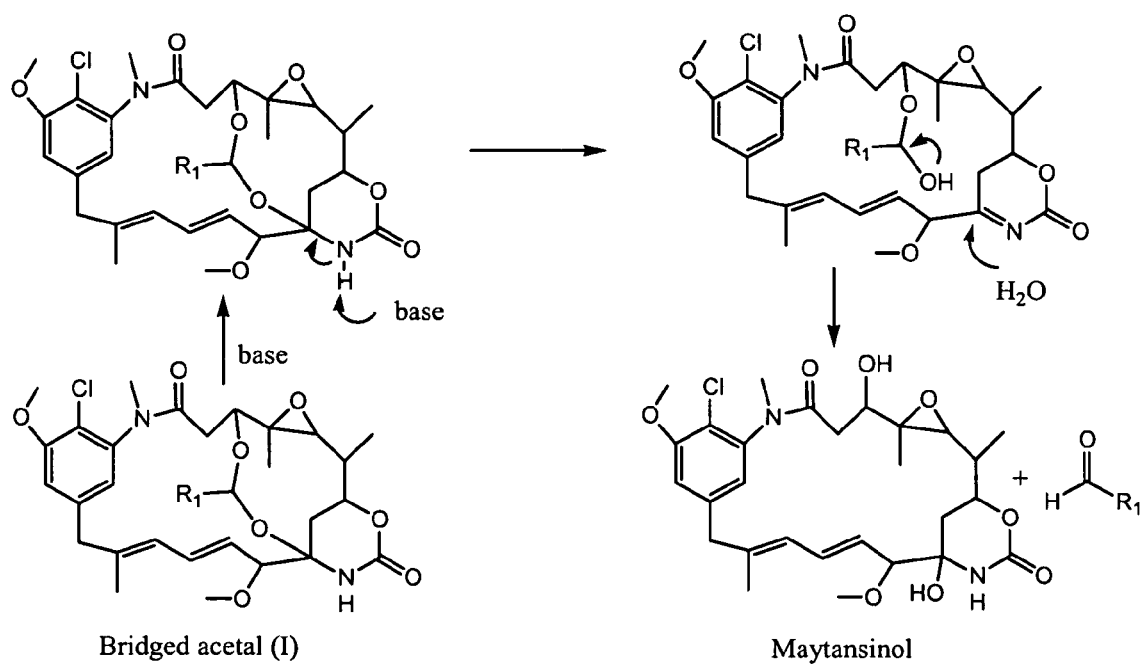
FIG. 4 shows a possible mechanism for the conversion of C3 to C9 bridged acetals of maytansinol to maytansinol. The bridged acetal is illustrated by the compound of general formula (I) as described herein.

While it is most convenient to convert the bridged acetal to maytansinol under basic conditions, the bridged acetal can also be converted under acidic conditions. Conversion of the bridged acetal to maytansinol under acidic conditions is not surprising as cleavage of acetal protecting groups is common in organic synthesis. While not wanting to be bound by any explanation, conversion of the bridged acetal to maytansinol by aqueous base is believed to occur by deprotonation of the cyclic carbamate with elimination of aldehyde, FIG. 4.

Once the bridged acetal is converted to maytansinol, the resulting maytansinol can be isolated by several means known to one skilled in the art. To prevent decomposition of the resulting maytansinol, the pH of the basic quenched mixture can be adjusted to between about 3 and about 9, most preferably to between about 4 and about 7 by adding an acid or aqueous buffer. Suitable acids include hydrochloric acid, phosphoric acid, trifluoroacetic acid, formic acid, and acetic acid. Of these, the preferred acids are formic acid and acetic acid as they give an easily filterable precipitate of aluminum-based byproducts.

Also, to aid in the isolation, aluminum-based byproducts can be precipitated at the adjusted pH by addition of a water immiscible solvent, such as, for example, ethyl acetate, butyl acetate or dichloromethane. The pH can be adjusted and the water immiscible solvent added simultaneously or these steps can be conducted separately and in either order. The acid and water immiscible solvent are added at equal to or below $0°$ C., preferably between $-20°$ C. and $-60°$ C., more preferably between $-25°$ C. to $-50°$ C., and most preferably between $-30°$ C. and $-40°$ C. to precipitate aluminum-based byproducts. The precipitated aluminum-based byproducts can be removed by several means known to one skilled in the art. For example the precipitate is easily filtered and the filtrate is found to be substantially free of bridged acetals of the C3-ester starting material.

As used herein, "substantially free" in this context indicates that less than 10% by weight of the bridged acetals of the starting C3-esters remains. More preferably, less than 5% of the bridged acetals remains, and most preferably less than 2% of the bridged acetals remains.

Alternatively, instead of precipitating the aluminum-based byproducts a strong acid such as hydrochloric acid or sulfuric acid can be added after the quench to adjust the pH to about 2 or less to dissolve the aluminum-based byproducts. Dissolving the aluminum-based byproducts allows efficient extraction of the aqueous phase. The amount of acid needed to dissolve the aluminum-based byproducts will depend on the concentration and type of acid used and the determination of these is within the skill of one of ordinary skill in the art.

The highly acidic conditions needed to dissolve aluminum based byproducts could potentially decompose a significant portion of the maytansinol. However since the extraction is efficient and solid aluminum-based byproducts are dissolved under the acidic conditions, a rapid extraction can be easily conducted. Use of a centrifugal extractor for example could allow the extraction to be conducted while exposing material to highly acidic conditions for only a few minutes or possibly seconds. A representative acidic centrifugal extraction has been used in the extraction of penicillin, Podbielniak, W. J., Kaiser, H. R., Ziegenhom, G. J. (1970) "Centrifugal solvent extraction In the History of Penicillin Production" Chem. Eng. Prog. Symp. Vol. 66 pages 44-50. One skilled in the art would know that the extent of decomposition of product under acidic conditions will depend on exposure time and that many methods are available for performing rapid extractions. The extracted maytansinol will be substantially free of bridged acetals of the C3-ester starting material.

A further aspect of the invention is to provide isolated C3 to C9 bridged acetals of maytansinol. The bridged acetal is in effect a form of maytansinol that has a protecting group on the C3 and C9 alcohols, so it can be used to prepare synthetic maytansinoid derivatives. Any maytansinol analogue, such as those described herein can have any of numerous bridge structures, including those described herein. Thus, one of ordinary skill in the art can readily envision numerous C3-C9 bridged acetals encompassed by the present invention.

Representative C3-C9 bridged acetals include compounds of Formula (I'):

Formula (I')

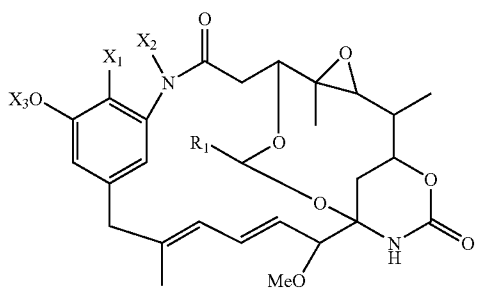

wherein:

$X_1$ represents H, Cl, or Br; $X_2$ represents H, or Me; $X_3$ represents H, Me, or $Me(CH_2)_pCOO$, wherein p is between 0-10; and $R_1$ represents alkyl, $CH(CH_3)N(CH_3)Q$, or $CH(CH_3)N(CH_3)COR_4$.

When $R_1$ is alkyl, the preferred alkyls are $C_1$-$C_4$ alkyl groups, such as $CH_3$, $CH_2CH_3$, $CH(CH_3)_2$, $CH_2CH_2CH_3$, $CH(CH_3)CH_2CH_3$, $CH_2CH(CH_3)_2$, and $(CH_2)_3CH_3$.

When $R_1$ is $CH(CH_3)N(CH_3)Q$, Q is H or Q represents an amino protecting group, many of which are described in "Protective groups in organic synthesis" 2nd Edition. Representative Q groups include but are not limited to sulfenamides such as S-alkyl and S-aryl, carbamates such as COO-alkyl, COO-aryl, $COOCH_2CH_2SiMe_3$, $COOCMe_3$, $COOCH_2CCl_3$, and $COOCH_2CF_3$, and silyl groups such as $SiMe_3$ and $SiMe_2$-tBu. When part of Q is alkyl, suitable alkyl groups include, but are not limited to, $C_1$-$C_{10}$ alkyl groups, such as methyl, ethyl, propyl, isopropyl, butyl, isobutyl, tert-butyl, cyclo pentyl and the like. Also, when part of Q is aryl, suitable aryl groups include, but are not limited to, simple or substituted aryl or heterocyclic with $C_1$-$C_{12}$, such as, phenyl, pyridyl, naphthyl.

When $R_1$ is $CH(CH_3)N(CH_3)COR_4$, $R_4$ is selected from alkyl, aryl or $(CH_2)_n(CR_6R_7)_mSV$, in which n represents 0-9, m represents 0-2, provided that n and m are not 0 at the same time; $R_6$ represents H, alkyl or aryl, $R_7$ represents H, alkyl or aryl, and V represents H, or a thiol protecting group, many of which are described in "Protective groups in organic synthesis" 2nd Edition. Representative thiol protecting groups include but are not limited to aryl, S-alkyl, S-aryl, $SiMe_3$, $SiMe_2$-tBu, $ArNO_2$, $Ar(NO_2)_2$, CO-alkyl, CO-aryl, wherein when part of V is an alkyl, suitable alkyl groups include, but are not limited to, linear alkyl, branched alkyl, or cyclic alkyl with $C_1$-$C_{10}$, such as methyl, ethyl, propyl, isopropyl, butyl, isobutyl, tert-butyl, cyclo pentyl and the like. Also, when part of V is an aryl, suitable aryl groups include, but are not limited to, simple or substituted aryl or heterocyclic with $C_1$-$C_{12}$, such as, phenyl, pyridyl, naphthyl. One skilled in the art will realize that the $R_1$ group present in the acetal side chain can be varied by reducing a C3-ester of maytansinol that has the corresponding C3-ester side chain.

For purposes of the groups represented by $R_4$, suitable alkyl groups include, but are not limited to, linear $C_1$-$C_{10}$ alkyl and branched or cyclic $C_3$-$C_{10}$ alkyl, such as methyl, ethyl, propyl, isopropyl, butyl, isobutyl, tert-butyl, cyclo pentyl and the like. Also, for purposes of the groups represented by $R_4$, suitable aryl groups include, but are not limited to, simple or substituted $C_3$-$C_{12}$ aryl or heterocyclic such as, phenyl, pyridyl, and naphthyl.

For purposes of groups represented by $R_6$ and $R_7$, suitable alkyl groups include, but are not limited to, linear $C_1$-$C_{10}$ alkyl groups, such as methyl, ethyl, propyl, isopropyl, butyl, isobutyl, tert-butyl, cyclo pentyl and the like. Also, for purposes of the groups represented by $R_6$ and $R_7$, suitable aryl groups include, but are not limited to, simple or substituted aryl or heterocyclic with $C_3$-$C_{12}$, such as, phenyl, pyridyl, and naphthyl.

In another aspect, the bridged acetal is represented by Formula (I):

Formula (I)

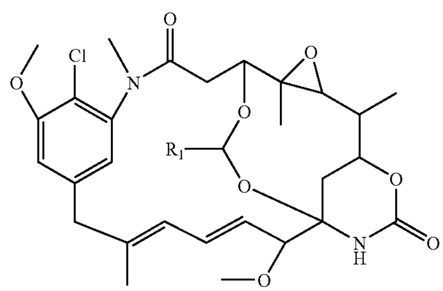

wherein $R_1$ is as defined above for formula (I').

The bridged acetals can be prepared as byproducts of the reduction of C3-esters of maytansinol as described above, and can be isolated by chromatography, such as, but not limited to, normal phase chromatography, silica chromatography, cyano-bonded silica chromatography or reverse phase chromatography. One such example of isolation is given in Example 3.

The isolated bridged acetal is converted to maytansinol by incubation with acid or base at a temperature ranging between about 40° C. to about −40° C. Typically, the reaction is conducted at an ambient temperature. The time needed for the reaction will depend on several factors, such as pH, temperature, scale of the reaction, and concentration, and can be monitored by HPLC. Suitable acids include hydrochloric acid, phosphoric acid, trifluroacetic acid, acetic acid and formic acid. Suitable bases include triethylamine, disopropylethylamine, NaOH or any strong base. For conversion under acidic conditions, the pH is adjusted to between about 1 and about 5, optimally to between about 2 and about 4. For conversion under basic conditions, the pH is adjusted to between about 8 and about 13, optimally to between about 9 and about 12.

Those of ordinary skill in the art will recognize and understand that functional equivalents of the procedures, processing conditions, and techniques illustrated herein can be used at a large scale (e.g., industrial). All such known equivalents are intended to be encompassed by this invention.

All references cited herein and in the examples that follow are expressly incorporated by reference in their entireties.

EXAMPLES

Materials and Methods

The present invention is further described by the following examples, which are illustrative of the process, and which should not be construed as limiting the invention. The process parameters given below can be adopted and adapted by skilled persons to suit their particular needs.

All reactions were performed under an argon atmosphere with magnetic stirring. Cooling bath temperatures were maintained using acetone as solvent and a NesLab CC-100 cooling unit. Tetrahydrofuran was purchased as an anhydrous solvent from Aldrich. C3-esters of maytansinol, such as ocins were produced as described in U.S. Pat. No. 6,790,954. D-DM1-SMe was prepared as described in U.S. Pat. No. 6,333,410. D-DM4-SMe was prepared as described in U.S. Patent Publication No. 20040235840. Nuclear magnetic resonance (NMR) spectra were obtained at 400 MHz using a Bruker ADVANCE™ series NMR. A Bruker ESQUIRE™ 3000 ion trap mass spectrometer was used to obtain mass spectra and was used either in line with or separate from an Agilent 1100 series HPLC. When applicable, samples were analyzed using the reversed phase analytical HPLC method described below. Also, when applicable, samples were purified using the preparative HPLC method described below. Analytical thin layer chromatographic (TLC) assays were performed using silica TLC plates and a mobile phase of dichloromethane:methanol 95:5 (v:v).

HPLC Method:

A. Analytical Reverse Phase HPLC Method:

Column: Kromasil C8 150×4.6 mm, 5 micron. Temperature: Ambient

Flow rate: 1.0 mL/min Injection volume: 4.0 microliters

| Time | % deionized water + 0.1% trifluoro acetic acid | % acetonitrile |
| --- | --- | --- |
| 0 | 63 | 37 |
| 15 | 58 | 42 |
| 25 | 42 | 58 |
| 35 | 32 | 68 |
| 36 | 63 | 37 |
| 43 | 63 | 37 |

B. Preparative Reverse Phase HPLC Method

Column: Kromasil C8 250×20 mm, 10 micron. Temperature: Ambient

Flow rate: 19 mL/min Injection volume: Typically between 0.1-0.2 mL

| Time | % deionized | % acetonitrile |
| --- | --- | --- |
| 0 | 63 | 37 |
| 15 | 58 | 42 |
| 25 | 42 | 58 |
| 35 | 32 | 68 |
| 36 | 63 | 37 |
| 43 | 63 | 37 |

EXAMPLE 1

Preparation of 0.67 M LiAl(OMe)$_3$H

A 200 mL three necked flask was equipped with a magnetic stir bar, and a thermometer. A 1 M lithium aluminum hydride solution of LiAlH$_4$ in tetrahydrofuran (71 mL, 71 mmol) and 26.8 mL of tetrahydrofuran were transferred to the flask via syringe. The flask was cooled in a −60° C. bath with stirring until the contents reached −43° C. A solution of 8.7 mL methanol (6.85 g, 214 mmol) in 8.0 mL of tetrahydrofuran was added drop-wise via a syringe while keeping the temperature of the contents between −40° C. and −45° C. The solution was stirred at −45° C. for an additional 10 min.

EXAMPLE 2

Preparation of LiAl(OMe)$_{2.5}$H$_{1.5}$

A 200 mL three necked flask was equipped with a magnetic stir bar and a thermometer. A 1 M lithium aluminum hydride solution of LiAlH$_4$ in tetrahydrofuran (71 mL, 71 mmol) and 28 mL of tetrahydrofuran were transferred to the flask via syringe. The flask was cooled in a −60° C. bath with stirring until the contents reached −43° C. A solution of 7.25 mL methanol (5.71 g, 178 mmol) in 8.0 mL of tetrahydrofuran was added drop-wise via a syringe while keeping the temperature of the contents between −40° C. and −45° C. The solution was stirred at −45° C. for an additional 10 min.

EXAMPLE 3

Preparation of the Bridged Acetal Compound Shown in Formula (I), R$_1$=CH(CH$_3$)$_2$ This example describes preparation of the bridged acetal compound shown in Formula (I), where R$_1$ is CH(CH$_3$)$_2$, reduction of ansamitocins with LiAl(OMe)$_3$H, followed by aqueous formic acid quench. Ansamitocins (3.0 g, 4.72 mmol) were weighed into a three necked flask equipped with a thermometer. Tetrahydrofuran (15 mL) was added to the flask with stirring, and the flask was cooled in a −57° C. cooling bath. Once the contents of the flask reached −35° C., a solution of 0.67 M LiAl(OMe)$_3$H in tetrahydrofuran (56 mL, 37.7 mmol) was added dropwise by syringe using a syringe pump. The temperature of the reaction was maintained between −30° C. and −40° C. throughout the addition. After addition was complete the reaction was stirred for 2 hours at between −34° C. and −37° C. A solution of 88% formic acid (1.85 mL, 2.16 g, 41.5 mmol) in 23 mL of deionized water was added dropwise to the flask at a rate that did not produce excessive frothing, followed by 66 mL of ethyl acetate. The cooling bath was removed and the mixture was allowed to warm to room temperature. The pH of the mixture was checked with pH paper and found to be approximately pH 6. Precipitated aluminum-based byproducts were removed by vacuum filtration and the solvent was removed from filtrate by rotary evaporation under vacuum. Butyl acetate (10 mL) was added to the residue, and the solvent was then evaporated in order to remove residual water. The residue was purified by silica chromatography using dichloromethane:methanol 95:5 (v:v) giving a later eluting band (maytansinol) and an early eluting band. The maytansinol band was collected and solvent was removed by rotary evaporation to give 1.55 g of maytansinol (58% yield by weight). Solvent was removed from the earlier eluting band, and the material was dissolved in a minimum volume of acetonitrile, then purified by preparative reverse phase HPLC. The compound of Formula (I) (retention time 26 min) was recovered, and solvent was removed by rotary evaporation to give 440 mg (15% yield by weight). Characterization of maytansinol: $^1$H NMR (CDCl$_3$) δ 0.83 (s, 3H), 1.20 (m, 1H), 1.30 (d, 3H, J=6.0 Hz), 1.50 (m, 2H), 1.69 (s, 3H), 2.10 (d, 1H, J=9.4 Hz), 2.52 (d, 1H, J=9.4 Hz), 2.88 (d, 1H, J=5.4 Hz), 3.12 (d, 1H, J=12.7 Hz), 3.2 (s, 3H), 3.36 (s, 3H), 3.46 (m, 2H), 3.54 (d, 1H, J=9.3), 3.64 (br s, 1H), 3.99 (s, 3H), 4.36 (dd, 1H, J=12, 1.0 Hz), 5.53 (dd, 1H, J=15, 9.3 Hz), 6.14 (d, 1H, J=11 Hz), 6.14 (d, 1H, J=11 Hz), 6.27 (s, 1H), 6.44 (dd, 1H, J=15, 11 Hz), 6.81 (d, 1H, J=1.8 Hz), 6.96 (d, 1H, J=1.8 Hz); Characterization of the compound of Formula (I): R$_1$=CH(CH$_3$)$_2$: $^1$H NMR (CDCl$_3$) δ 0.78 (s, 3H), 0.97 (d, 3H, J=6.9), 1.04 (d, 3H, J=6.7), 1.23 (m, 1H), 1.28 (d, 3H, J=6.4), 1.54 (m, 1H), 1.66 (s, 3H), 1.72 (m, 2H) 2.03 (dd, 1H, J=14, 3.6 Hz), 2.3 (d, 1H, J=14), 2.49 (dd, 1H, J=11.7, 14), 2.92 (d, 1H, J=9.5 Hz), 3.14 (s, 3H), 3.12 (m, 1H), 3.37, (s, 3H), 3.52 (m, 3H), 3.65 (m, 1H), 3.75 (m, 1H), 3.97 (s, 1H), 4.31 (m, 2H), 5.52 (dd, 1H, J=16, 8.7 Hz), 6.13 (d, 1H, J=11 Hz), 6.34 (s, 1H), 6.45 (dd, 1H, J=16, 11 Hz), 6.80 (d, 1H, J=1.5 Hz), 6.92 (d, 1H, J=1.5 Hz); MS (M+1 found: 619.3 M+1 calculated: 619.2)

EXAMPLE 4

Conversion of the Compound of Formula (I), R$_1$=CH(CH$_3$)$_2$ to Maytansinol Under Basic Conditions (pH 11) at Ambient Temperature This example describes conversion of the compound of Formula (I), where R$_1$ is CH(CH$_3$)$_2$, to maytansinol under basic conditions (pH 11) at ambient temperature. Diisopropyl ethyl amine was added to a solution of 30 mL tetrahydrofuran and 10 mL deionized water while monitoring the pH using a pH meter until a pH of 11 was obtained. The compound of Formula (I) (3.0 mg, mmol) prepared in Example 3 was dissolved in 1.5 mL of pH 11 tetrahydrofuran/water solution at ambient temperature and mixed well. The solution was analyzed by HPLC/MS at various time points. The retention time of the product and the mass spectrum matched that of authentic maytansinol. Conversion was approximately ½ complete after 15 min.

EXAMPLE 5

Conversion of the Bridged Acetals of Formula (I) to Maytansinol Under Acidic Conditions (pH 2.0) at Ambient Temperature Trifluoroacetic acid was added to a solution of 30 mL tetrahydrofuran and 10 mL deionized water while monitoring the pH using a pH meter until a pH of 2.0 was obtained. The compound of Formula (I) (3.0 mg, mmol) was dissolved in 1.5 mL of the pH 2 tetrahydrofuran/water solution at ambient temperature and mixed well. The solution was analyzed by HPLC/MS at various time points. The retention time of the product and the mass spectrum matched that of authentic maytansinol. Conversion was approximately ½ complete after 1 hour.

EXAMPLE 6

An Assay for Determining the Percent Conversion of the Bridged Acetals of Formula (I) to Maytansinol Approximately 0.2 mL of the reaction mixture was quickly added to a test tube containing 0.3 mL water, 0.05 mL acetic acid and 1 mL ethyl acetate and mixed well. The resulting mixture did not convert the bridged acetal of Formula (I) to maytansinol at any appreciable rate. The organic layer along with authentic maytansinol, ansamitocins and the compound of Formula (I) were analyzed by thin layer chromatography using dichloromethane: methanol 95:5 (v:v). Bands from the worked up reaction mixture were identified if they co-migrated with one of the authentic compounds. The organic layer was also analyzed by first diluting with one volume of acetonitrile and analyzing by reverse phase HPLC. Retention times of authentic ansamitocins, maytansinol and the compound of Formula (I) were determined at 16.2 min, 8.7 min, and 16.9 min respectively.

EXAMPLE 7

Reduction of Ansamitocins with LiAl(OMe)$_3$H Using Water Followed by Aqueous Formic Acid Quench to give Maytansinol Ansamitocins (3.0 g, 4.72 mmol) were weighed into a three necked flask equipped with a thermometer. Tetrahydrofuran (15 mL) was added to the flask with stirring and the flask was cooled in a −50° C. cooling bath. Once the contents of the flask reached −35° C., a solution of 0.67 M LiAl(OMe)$_3$H in tetrahydrofuran (56 mL, 37.7 mmol) was added dropwise by syringe using a syringe pump. The temperature of the reaction was maintained between −30° C. and −40° C. throughout the addition. After addition was complete, the reaction was stirred for 2 hours at between −32° C. and −37° C. Deionized water (7.7 mL) was added dropwise to the −35° C. reaction to give a basic quenched mixture. The basic quenched mixture was analyzed after set holding periods by the thin layer chromatography assay described in Example 6. The compound of Formula (I) was detected after holding for 5 and 15 minutes. After 30 min a sample of the basic quenched mixture was analyzed again by the thin layer chromatography method. The compound of Formula (I) was no longer detected. Aqueous formic acid (deionized water, 15 mL and 88% formic acid, 1.85 mL) was then added to the flask followed by 66 mL of ethyl acetate. The cooling unit was turned off, and the mixture was allowed to slowly warm to room temperature. The pH of the mixture was checked with pH paper and found to be approximately pH 6. The precipitated aluminum byproducts were removed by vacuum filtration. Solvent was evaporated from the filtrate by rotary evaporation under vacuum. Butyl acetate was added to the residue, the solvent was then evaporated to remove any remaining water The residue was purified by silica chromatography using a mobile phase of dichloromethane:methanol 95:5 (v:v) to give 2.2 g of maytansinol (85% yield by weight).

EXAMPLE 8

Reduction of Ansamitocins with LiAl(OMe)$_{2.5}$H$_{1.5}$ Followed by Aqueous Quenching and pH Neutralization with Formic Acid This example describes reduction of ansamitocins with LiAl(OMe)$_{2.5}$H$_{1.5}$ using water followed by aqueous formic acid quench. Ansamitocins (1.0 g, 1.57 mmol) were weighed into a three necked flask equipped with a thermometer. Tetrahydrofuran (5 mL) was added to the flask with stirring, and the flask was cooled in a −50° C. cooling bath. Once the contents of the flask reached −35° C., a solution of 0.67 M LiAl(OMe)$_3$H in tetrahydrofuran (18.5 mL, 12.4 mmol) was added dropwise by syringe using a syringe pump. The temperature of the reaction was maintained between −30° C. and −40° C. throughout the addition. After addition was complete the reaction was stirred for 2 hours at between −32° C. and −37° C. Deionized water (2.5 mL) was added dropwise to the −35° C. reaction to give a basic quenched mixture. The basic quenched mixture was analyzed by the thin layer chromatography assay described in example 6. The compound of Formula (I) was detected. After 30 min the basic quenched mixture was analyzed again by the thin layer chromatography method. The compound of Formula (I) was no longer detected. Aqueous formic acid (deionized water, 5 mL, and 88% formic acid, 0.62 mL) was then added to the flask followed by 22 mL of ethyl acetate. The cooling unit was turned off and the mixture was allowed to slowly warm to room temperature. The pH of the mixture was checked with pH paper and found to be approximately pH 6. The mixture was vacuum filtered, and solvent was removed by rotary evaporation under vacuum. Butyl acetate (5 mL) was added to the residue, the solvent was then evaporated to remove any remaining water. The residue was purified by silica chromatography using a mobile phase of dichloromethane:methanol 95:5 (v:v) to give 0.63 g of maytansinol (71% yield by weight).

EXAMPLE 9

Reduction of Ansamitocins with LiAl(OMe)$_3$H Followed by Aqueous Quenching and Acidification with HCl This example describes reduction of ansamitocins with LiAl(OMe)$_3$H using water followed by aqueous HCl. Ansamitocins (200 mg, 0.32 mmol) were weighed into a 25 mL round bottomed flask. Tetrahydrofuran (1.0 mL) was added to the flask with stirring, and the flask was cooled in a −42° C. cooling bath. After 10 min, a solution of 0.67 M LiAl(OMe)$_3$H in tetrahydrofuran (3.8 mL, 2.52 mmol) was added dropwise by syringe. The bath temperature was maintained between −34° C. and −42° C. throughout the addition. After addition was complete, the reaction was stirred for 2 hours at between −32° C. and −37° C. 1 mL of deionized water was added dropwise to the reaction. After a 30 min holding period, 2 mL of 3 M HCl and 10 mL of ethyl acetate were quickly added to the flask. The cooling unit was turned off, and most of the aluminum byproducts went into solution. The contents were transferred to a separatory funnel and mixed well. The organic layer was retained and washed with 2 mL of saturated sodium chloride. The organic layer was dried over anhydrous sodium sulfate, and solvent was removed by rotary evaporation. The residue was purified by silica chromatography using a mobile phase of dichloromethane:methanol 95:5 (v:v) to give 117 mg of maytansinol (66% yield by weight).

EXAMPLE 10

Reduction of D-DM1-SMe to Maytansinol

This example describes reduction of D-DM1-SMe, shown in FIG. 2, to maytansinol. D-DM1-SMe (10.0 g, 12.7 mmol) was weighed into a three necked flask equipped with a thermometer. Tetrahydrofuran (40.5 mL) was added to the flask with stirring, and the flask was cooled in a −50° C. cooling bath. Once the contents of the flask reached −35° C., a solution of 0.67 M LiAl(OMe)$_3$H in tetrahydrofuran (150 mL, 100 mmol) was added dropwise by syringe using a syringe pump. The temperature of the reaction was maintained between −30° C. and −40° C. throughout the addition. After addition was complete, the reaction was stirred for 2 hours at between −32° C. and −37° C. Deionized water (20 mL) was added dropwise to the −35° C. reaction to give a basic quenched mixture. After 30 min, aqueous formic acid (deionized water, 40 mL and 88% formic acid, 5.0 mL) was added to the flask, followed by 180 mL of ethyl acetate. The cooling unit was turned off, and the mixture was allowed to slowly warm to room temperature. The pH of the mixture was checked with pH paper and found to be approximately pH 6. The mixture was vacuum filtered, and solvent was removed by rotary evaporation under vacuum. Butyl acetate (25 mL) was added to the residue, the solvent was then evaporated to remove any remaining water. The residue was purified by silica chromatography using a mobile phase of dichloromethane:methanol 95:5 (v:v) to give 4.83 g of maytansinol. (67% yield by weight).

EXAMPLE 11

Reduction of D-DM4-SMe to Maytansinol

This example describes reduction of D-DM4-SMe, shown in FIG. 2, to maytansinol. D-DM4-SMe (501 mg, 0.60 mmol) was weighed into a three necked flask equipped with a thermometer. Tetrahydrofuran (2.0 mL) was added to the flask with stirring and the flask was cooled in a −50° C. cooling bath. Once the contents of the flask reached −35° C., a solution of 0.67 M LiAl(OMe)$_3$H in tetrahydrofuran (7.1 mL, 4.75 mmol) was added dropwise by syringe using a syringe pump. The temperature of the reaction was maintained between −30° C. and −40° C. throughout the addition. After addition was complete, the reaction was stirred for 2 hours at between −32° C. and −37° C. Deionized water (1 mL) was added dropwise to the −35° C. reaction to give a basic quenched mixture. After 30 min, aqueous formic acid (deionized water, 2.0 mL and 88% formic acid, 0.24 mL) was added to the flask followed by 9 mL of ethyl acetate. The cooling unit was turned off, and the mixture was allowed to slowly warm to room temperature. The mixture was vacuum filtered, and solvent was removed by rotary evaporation under vacuum. Butyl acetate (2 mL) was added to the residue, the solvent was then evaporated to remove any remaining water. The residue was purified by silica chromatography using a mobile phase of dichloromethane:methanol 95:5 (v:v) to give 443 mg of maytansinol (65% yield by weight).

What is claimed is:
1. A process for preparing maytansinol comprising:
   a) reducing a C3-ester of maytansinol with an aluminum-based hydride reducing reagent;
   b) quenching the reduction reaction; and
   c) subjecting the quenched mixture to a holding step; wherein said holding step converts C3 to C9 bridged acetal into maytansinol.
2. The process of claim 1, further comprising adjusting the pH of the quenched mixture after the holding step to between about 3 and about 9 and adding a water immiscible solvent, wherein said adjusting the pH and adding a water immiscible solvent are conducted simultaneously or in either order.
3. The process of claim 2, wherein the pH is adjusted by adding an acid or aqueous buffer.
4. The process of claim 3, wherein the acid is selected from a group consisting of acetic acid, formic acid, hydrochloric acid, phosphoric acid and trifluoroacetic acid.
5. The process of claim 2, wherein the water immiscible solvent is selected from the group consisting of ethyl acetate, dichloromethane and butyl acetate.

6. The process of claim 1, further comprising adjusting the pH of the quenched mixture after the holding step to about 2 or less.

7. The process of claim 1, wherein the holding step comprises maintaining the quenched mixture at a temperature of about −15° C. to about −50° C. for a period of at least about 0.25 to about 5 hours.

8. The process of claim 1 or 2, wherein the aluminum-based hydride reducing agent is selected from the group consisting of $LiAlH_4$, $LiAl(OMe)_3H$, $LiAl(OMe)_{2.5}H_{1.5}$, and sodium bis(2-methoxyethoxy)aluminum hydride.

9. The process of claim 8, wherein the aluminum-based hydride reducing agent is $LiAl(OMe)_3H$.

10. The process of claim 1 or 2, wherein the reduction reaction is quenched with water.

11. The process of claim 1 or 2, wherein the reduction reaction is quenched with an aqueous salt solution.

12. The process of claim 10, wherein the aqueous salt solution is a saturated solution of sodium chloride.

13. The process of claim 1, wherein the C3 to C9 bridged acetal is a compound of formula (I):

Formula (I)

wherein, $R_1$ represents alkyl, $CH(CH_3)N(CH_3)Q$, or $CH(CH_3)N(CH_3)COR_4$; Q represents H or an amino protecting group; and $R_4$ represents alkyl, aryl or $(CH_2)_n(CR_6R_7)_mSV$, in which n represents 0-9, m represents 0-2, provided m and n are not 0 at the same time, $R_6$ represents H, alkyl or aryl, $R_7$ represents H, alkyl or aryl, and V represents H or a thiol protecting group.

14. The process of claim 13, wherein said alkyl represented by $R_1$ is $CH_3$, $CH_2CH_3$, $CH(CH_3)_2$, $CH_2CH_2CH_3$, $CH(CH_3)CH_2CH_3$, $CH_2CH(CH_3)_2$, or $(CH_2)_3CH_3$.

15. The process of claim 13, wherein when $R_1$ is $CH(CH_3)N(CH_3)Q$.

16. The process of claim 15, wherein Q represents an amino protecting group selected from the group consisting of sulfenamide groups, carbamate groups and silyl groups.

17. The process of claim 13, wherein when $R_1$ is $CH(CH_3)N(CH_3)COR_4$.

18. The process of claim 17, wherein $R_4$ is $(CH_2)_n(CR_6R_7)_mSV$, in which n represents 0-9, m represents 0-2, provided m and n are not 0 at the same time, and V is a thiol protecting group selected from the group consisting of aryl, S-alkyl, S-aryl, $SiMe_3$, $SiMe_2$-tBu, $ArNO_2$, $Ar(NO_2)_2$, CO-alkyl, and CO-aryl.

19. The process of claim 17, wherein R4 is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

20. An isolated C3 to C9 bridged acetal of a C3-ester of maytansinol, which is a compound of formula (I'):

Formula (I')

Wherein:
$X_1$ represents H, Cl, or Br; $X_2$ represents H, or Me; $X_3$ represents H, Me, or $Me(CH_2)_pCOO$, wherein p is between 0-10; and $R_1$ represents alkyl, $CH(CH_3)N(CH_3)Q$, or $CH(CH_3)N(CH_3)COR_4$; Q represents H or an amino protecting group; and $R_4$ represents alkyl, aryl or $(CH_2)_n(CR_6R_7)_mSV$, in which n represents 0-9, m represents 0-2, provided m and n are not 0 at the same time, $R_6$ represents H, alkyl or aryl, $R_7$ represents H, alkyl or aryl, and V represents H or a thiol protecting group.

21. The isolated C3 to C9 bridged acetal of claim 20, which is a compound of formula (I):

Formula (I)

wherein, $R_1$ represents alkyl, $CH(CH_3)N(CH_3)Q$, or $CH(CH_3)N(CH_3)COR_4$; Q represents H or an amino protecting group; and $R_4$ represents alkyl, aryl or $(CH_2)_n(CR_6R_7)_mSV$, in which n represents 0-9, m represents 0-2, provided m and n are not 0 at the same time, $R_6$ represents H, alkyl or aryl, $R_7$ represents H, alkyl or aryl, and V represents H or a thiol protecting group.

22. The compound of claim 20 or 21, wherein said alkyl represented by $R_1$ is $CH_3$, $CH_2CH_3$, $CH(CH_3)_2$, $CH_2CH_2CH_3$, $CH(CH_3)CH_2CH_3$, $CH_2CH(CH_3)_2$, or $(CH_2)_3CH_3$.

23. The compound of claim 20 or 21, wherein when $R_1$ is $CH(CH_3)N(CH_3)Q$.

24. The compound of claim 20 or 21, wherein Q represents an amino protecting group selected from the group consisting of sulfenamide groups, carbamate groups and silyl groups.

25. The compound of claim 20 or 21, wherein when $R_1$ is $CH(CH_3)N(CH_3)COR_4$.

26. The compound of claim 25, wherein $R_4$ is $(CH_2)_n(CR_6R_7)_mSV$, and V is a thiol protecting group selected from the group consisting of aryl, S-alkyl, S-aryl, $SiMe_3$, $SiMe_2$-tBu, $ArNO_2$, $Ar(NO_2)_2$, CO-alkyl, and CO-aryl.

27. The compound of claim 25, wherein $R_4$ is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

28. A process for preparing an isolated C3 to C9 bridged acetal of a C3-ester of maytansinol comprising:
   a) reducing a C3-ester of maytansinol with an aluminum-based hydride reducing agent;
   b) quenching the reduction reaction, to thereby form a C3 to C9 bridged acetal of said C3-ester of maytansinol; and
   c) isolating the bridged acetal.

29. The process of claim 28, wherein the isolating is by chromatography.

30. The process of claim 29, wherein the chromatography is normal phase chromatography or reverse phase chromatography.

31. The process of claim 28, wherein the bridged acetal is a compound of formula (I):

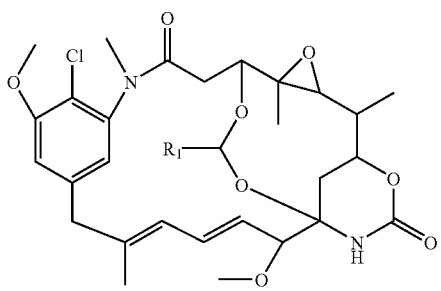

Formula (I)

wherein, $R_1$ represents alkyl, $CH(CH_3)N(CH_3)Q$, or $CH(CH_3)N(CH_3)COR_4$; Q represents H or an amino protecting group; and $R_4$ represents alkyl, aryl or $(CH_2)_n(CR_6R_7)_mSV$, in which n represents 0-9, m represents 0-2, provided m and n are not 0 at the same time, $R_6$ represents H, alkyl or aryl, $R_7$ represents H, alkyl or aryl, and V represents H or a thiol protecting group.

32. The process of claim 28 or 31, wherein the aluminum-based hydride reducing agent is selected from the group consisting of $LiAlH_4$, $LiAl(OMe)_3H$, $LiAl(OMe)_{2.5}H_{1.5}$, and sodium bis(2-methoxyethoxy)aluminum hydride.

33. The process of claim 32, wherein the aluminum-based hydride reducing agent is $LiAl(OMe)_3H$.

34. The process of claim 28 or 31, wherein the reduction reaction is quenched with water.

35. The process of claim 28 or 31, wherein the reduction reaction is quenched with an aqueous salt solution.

36. The process of claim 35, wherein the aqueous salt solution is a saturated solution of sodium chloride.

37. The process of claim 35, wherein the aqueous salt solution is a solution of sodium potassium tartrate.

38. The process of claim 31, wherein said alkyl represented by $R_1$ is $CH_3$, $CH_2CH_3$, $CH(CH_3)_2$, $CH_2CH_2CH_3$, $CH(CH_3)CH_2CH_3$, $CH_2CH(CH_3)_2$, or $(CH_2)_3CH_3$.

39. The process of claim 31, wherein when $R_1$ is $CH(CH_3)N(CH_3)Q$.

40. The process of claim 38, wherein Q represents an amine protecting group, selected from the group consisting of sulfenamide groups, carbamate groups and silyl groups.

41. The process of claim 31, wherein when $R_1$ is $CH(CH_3)N(CH_3)COR_4$.

42. The process of claim 41, wherein $R_4$ is $(CH_2)_n(CR_6R_7)_mSV$, and V is a thiol protecting group selected from the group consisting of aryl, S-alkyl, S-aryl, $SiMe_3$, $SiMe_2$-tBu, $ArNO_2$, $Ar(NO_2)_2$, CO-alkyl, and CO-aryl.

43. The process of claim 41, wherein $R_4$ is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

44. A process for converting a C3 to C9 bridged acetal of a C3-ester of maytansinol to maytansinol comprising incubating the bridged acetal with an acid or a base.

45. The process of claim 44, wherein the acid is hydrochloric acid, phosphoric acid, trifluoroacetic acid, acetic acid, or formic acid.

46. The process of claim 44, wherein the base is triethylamine, diisopropyl-ethyamine, NaOH or a strong base.

47. The process of claim 44, wherein the incubating is at a temperature of about 40° C. to about −40° C.

48. The process of claim 31, wherein the bridged acetal is a compound of formula

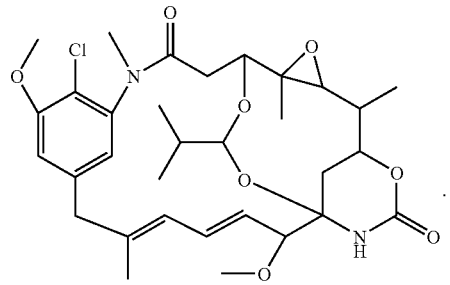

* * * * *

UNITED STATES PATENT AND TRADEMARK OFFICE
CERTIFICATE OF CORRECTION

PATENT NO.        : 7,411,063 B2
APPLICATION NO.   : 11/594156
DATED             : August 12, 2008
INVENTOR(S)       : Ravi V.J. Chari and Wayne C. Widdison It is certified that error appears in the above-identified patent and that said Letters Patent is hereby corrected as shown below:

Please delete Figure 2 and replace with the following Figure 2:

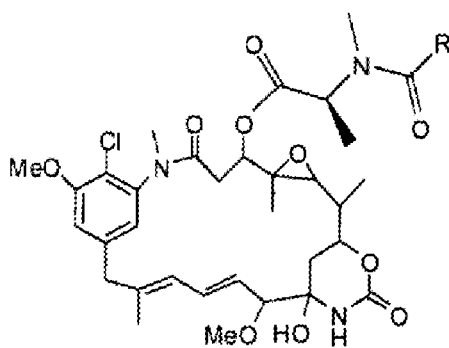

Maytansine R = CH₃
L-DM1 R = CH₂CH₂SH
L-DM4 R = CH₂CH₂C(CH₃)₂SH

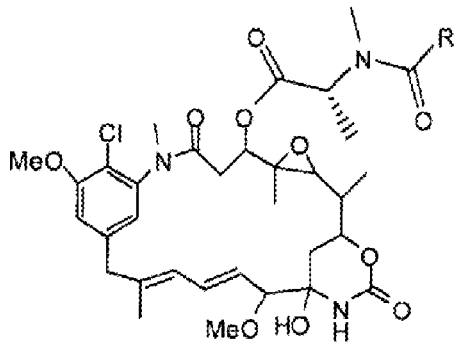

unnatural N-methyl-D-alanine side chain
R = CH₃
D-DM1 R = CH₂CH₂SH
D-DM4 R = CH₂CH₂C(CH₃)₂SH

UNITED STATES PATENT AND TRADEMARK OFFICE
CERTIFICATE OF CORRECTION

PATENT NO. : 7,411,063 B2
APPLICATION NO. : 11/594156
DATED : August 12, 2008
INVENTOR(S) : Ravi V.J. Chari and Wayne C. Widdison It is certified that error appears in the above-identified patent and that said Letters Patent is hereby corrected as shown below:

Please correct claims 19, 27, 43 and 46 as follows:
Col. 15 Claim 19. The process of claim 17, wherein $R_4$ is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

Col. 17 Claim 27. The compound of claim 25, wherein $R_4$ is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

Col. 18 Claim 43. The process of claim 41, wherein $R_4$ is $CH_2CH_2SH$, $CH_2CH_2SSCH_3$, $CH_2CH_2CH(CH_3)SH$, $CH_2CH_2CH(CH_3)_2SSCH_3$, $CH_2CH_2C(CH_3)_2SH$, or $CH_2CH_2C(CH_3)_2SSCH_3$.

Col. 18 Claim 46. The process of claim 44, wherein the base is triethylamine, diisopropyl ~~ethyamine~~ethylamine, NaOH or a strong base.

Signed and Sealed this

Thirtieth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,411,063 B2
APPLICATION NO. : 11/594156
DATED : August 12, 2008
INVENTOR(S) : Ravi V.J. Chari and Wayne C. Widdison It is certified that error appears in the above-identified patent and that said Letters Patent is hereby corrected as shown below:

Please delete Figure 2 and replace with the following Figure 2:

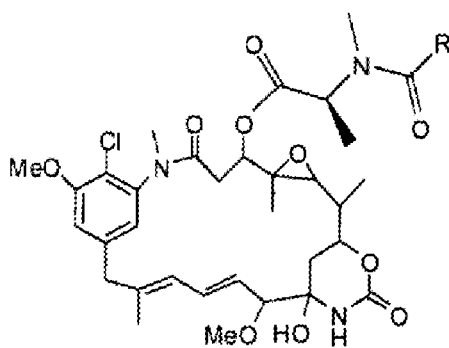

Maytansine R = $CH_3$
L-DM1 R = $CH_2CH_2SH$
L-DM4 R = $CH_2CH_2C(CH_3)_2SH$

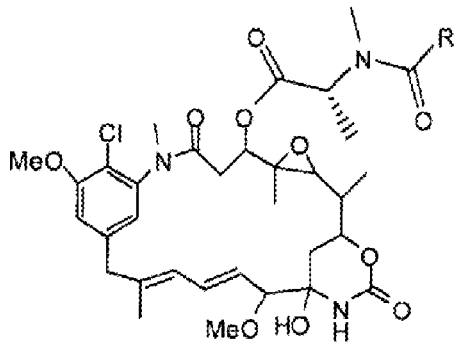

unnatural N-methyl-D-alanine side chain
R = $CH_3$
D-DM1 R = $CH_2CH_2SH$
D-DM4 R = $CH_2CH_2C(CH_3)_2SH$

UNITED STATES PATENT AND TRADEMARK OFFICE
CERTIFICATE OF CORRECTION

PATENT NO. : 7,411,063 B2
APPLICATION NO. : 11/594156
DATED : August 12, 2008
INVENTOR(S) : Ravi V.J. Chari and Wayne C. Widdison It is certified that error appears in the above-identified patent and that said Letters Patent is hereby corrected as shown below:

Please correct claims 19, 27, 43 and 46 as follows:
Col. 15 Claim 19, lines 62-65 should read.  The process of claim 17, wherein $R_4$ is $CH_2CH_2SH$, $CH_2CH_2SSCH_3$, $CH_2CH_2CH(CH_3)SH$, $CH_2CH_2CH(CH_3)$~~2~~$SSCH_3$, $CH_2CH_2C(CH_3)_2SH$, or $CH_2CH_2C(CH_3)_2SSCH_3$.

Col. 17 Claim 27, lines 1-3 should read.  The compound of claim 25, wherein $R_4$ is $CH_2CH_2SH$, $CH_2CH_2SSCH_3$, $CH_2CH_2CH(CH_3)SH$, $CH_2CH_2CH(CH_3)$~~2~~$SSCH_3$, $CH_2CH_2C(CH_3)_2SH$, or $CH_2CH_2C(CH_3)_2SSCH_3$.

Col. 18 Claim 43, lines 20-22 should read.  The process of claim 41, wherein $R_4$ is $CH_2CH_2SH$, $CH_2CH_2SSCH_3$, $CH_2CH_2CH(CH_3)SH$, $CH_2CH_2CH(CH_3)$~~2~~$SSCH_3$, $CH_2CH_2C(CH_3)_2SH$, or $CH_2CH_2C(CH_3)_2SSCH_3$.

Col. 18 Claim 46, lines 29-30 should read.  The process of claim 44, wherein the base is triethylamine, diisopropyl ~~ethyamine~~ethylamine, NaOH or a strong base.

This certificate supersedes the Certificate of Correction issued September 30, 2008.

Signed and Sealed this

Twenty-first Day of October, 2008

JON W. DUDAS
*Director of the United States Patent and Trademark Office*